United States Patent
Ott et al.

(10) Patent No.: US 9,675,074 B2
(45) Date of Patent: *Jun. 13, 2017

(54) METHODS TO REDUCE COLD DAMAGE IN CEREALS

(71) Applicant: Valent BioSciences Corporation, Libertyville, IL (US)

(72) Inventors: Eric Ott, Greenfield, IN (US); Franklin Paul Silverman, Highland Park, IL (US); Xiaozhong Liu, Vernon Hills, IL (US)

(73) Assignee: Valent BioSciences LLC, Libertyville, IL (US)

( * ) Notice: Subject to any disclaimer, the term of this patent is extended or adjusted under 35 U.S.C. 154(b) by 20 days.

This patent is subject to a terminal disclaimer.

(21) Appl. No.: 14/750,045

(22) Filed: Jun. 25, 2015

(65) Prior Publication Data

US 2015/0373983 A1    Dec. 31, 2015

Related U.S. Application Data

(60) Provisional application No. 62/018,060, filed on Jun. 27, 2014.

(51) Int. Cl.
  *A01N 43/16* (2006.01)
  *A01N 45/00* (2006.01)
  *A01N 43/12* (2006.01)

(52) U.S. Cl.
  CPC ............ *A01N 45/00* (2013.01); *A01N 43/12* (2013.01)

(58) Field of Classification Search
  None
  See application file for complete search history.

(56) References Cited

U.S. PATENT DOCUMENTS

| 4,169,717 A * | 10/1979 | Ashmead | A01N 37/44 504/126 |
| 5,188,655 A * | 2/1993 | Jones | A01N 43/90 504/136 |
| 2008/0318782 A1 | 12/2008 | Fugiel et al. | |

OTHER PUBLICATIONS

International Search Report issued in counterpart application No. PCT/US15/37633 issued Oct. 1, 2015.
Edgerton, "Some effect of gibberellin and growth retardants on bud development and cold hardiness of peach", American Society for Horticultural Science v. 88, pp. 197-203.
Yarushnykov et al., "Alleviation of frost damage to pear flowers by application of gibberellin", Plant Growth Regulation, 2005, 45, pp. 21-27.
Tranel, "Morphology and plasticity of maize (*Zea mays* L.) male inflorescence development and pollen production", Iowa State University, 2007, 105 pages.
Brok, "Effect of gibberrellic acid on frost tolerance of locust and common alder seedlings", Bulletin of the Latvian Academy of Sciences, No. 8(193), Mar. 30, 1963, pp. 1-9.

* cited by examiner

*Primary Examiner* — Alton Pryor
(74) *Attorney, Agent, or Firm* — Wood, Phillips, Katz, Clark & Mortimer

(57) ABSTRACT

The present invention is directed to methods for improving cold temperature damage recovery of a cereal grain comprising applying an effective amount of at least one gibberellin to the cereal grain during early vegetative growth stage. The present invention is also directed to methods for improving yield of a cereal grain comprising applying an effective amount of at least one gibberellin to a cereal grain suffering from cold temperature damage during the early vegetative growth stage.

8 Claims, No Drawings

METHODS TO REDUCE COLD DAMAGE IN CEREALS

FIELD OF THE INVENTION

The present invention is generally directed to methods for improving cold damage recovery and yield of cereal grains comprising applying an effective amount of at least one gibberellin to the cereal grain foliage during an early vegetative growth stage.

BACKGROUND OF THE INVENTION

Crop growers desire to plant their crops as early as possible so that they can obtain the highest available yield during the growing season. Crop growers with a large acreage to plant also want to begin planting as soon as possible. Early planting, however, is not without risks. One risk is that the crops will be exposed to cold temperatures that may cause the seedlings or plants to suffer damage or death. Cold temperatures cause millions of dollars of damage to crops each year. In some parts of the United States, cold temperatures can occur at any time during the growing season. Cold temperature damage is most common, however, in the Spring when the plants are vulnerable.

Unfortunately if cold temperature damage occurs to a grower's crops, the grower is then faced with a dilemma. Currently growers must either replant their fields immediately, or wait for several days to see if their plants recover and then decide if they should replant their fields. If the growers wait for several days to see if their plants recover and the damaged plants do not, then they have wasted valuable time before replanting and further reduced their potential yields. If the plants appear to recover and the growers do not replant, then the growers will be concerned about the negative impacts on yield for the rest of the growing season. If the growers replant their crops, then they are spending valuable resources on damage mitigation that could have been spent elsewhere.

Accordingly, there is a need for new methods to assist growers when cold temperature damage occurs. The method should be easy to administer and provide excellent cold temperature damage recovery. The method should provide increased yield when the crops are damaged by cold temperatures.

SUMMARY OF THE INVENTION

In one aspect, the present invention is directed to methods for improving cold temperature damage recovery of a cereal grain comprising applying an effective amount of at least one gibberellin to the cereal grain during the early vegetative growth stage.

In a further aspect, the present invention is directed to methods for improving yield of a cereal grain that is or will be exposed to a cold temperature comprising applying an effective amount of at least one gibberellin to the cereal grain during the early vegetative growth stage.

DETAILED DESCRIPTION OF THE INVENTION

Unexpectedly, Applicants found that when a gibberellin was applied to cereal grains during the early vegetative stage, the cereal grains had greater yield and improved recovery from cold damage. Applicants' methods provide an answer to growers needs for a quick and effective treatment to reduce yield losses due to cold temperatures. Applicants' methods also allow growers to plant cereals even earlier then before because the risk of potential expensive yield losses due to cold weather is reduced.

Specifically, Applicants were surprised that when they applied gibberellic acid ("GA3") to corn plants by foliar spray applications during the V2 and V3 growth stages the plants recovered from cold temperature damage. This was unexpected because one skilled in the art would not have predicted that GA3 application would increase recovery from a cold or freezing event because GA3 provides protection from drought stress in corn.

The gibberellins may be applied to the cereals before or after they are exposed to cold temperatures. For example, a grower could apply gibberellin in anticipation of cold temperatures. Alternatively, the grower could apply the gibberellin to the damaged plants after the cold temperatures occur.

Gibberellins are naturally-occurring plant hormones involved in most phases of plant growth and development including germination, cell proliferation, cell elongation, bud break, flowering, sex determination, fruit set, seed development and senescence (reviewed in Olszewski et al., *Gibberellin Signaling: Biosynthesis, Catabolism, and Response Pathways*, The Plant Cell, S61-S80, Supplement 2002). GA3 is well-known for its promotion of plant growth and has been used in agriculture since the early 1960's. The major commercial uses of gibberellins include thinning and sizing of seedless table grapes, enhancement of fruit size and firmness, stimulation of growth and increased yield of pasture grasses, promotion of fruit set, and advancement of flowering in horticultural crops (Sponsel, *A Companion to Plant Physiology*, Fifth Edition by Lincoln Taiz and Eduardo Zeiger, available at http://5e.plantphys.net/article.php?ch=0&id=372, 2010).

Many authors have established that gibberellins can mitigate freeze damage to other types of crops. For example, gibberellins may alleviate freeze damage to pear, black locust, black alder, peach, and assist with cold resistance in vegetables. See Vladymyr V. Yarushnykov, Michael M. Blanke, *Alleviation of frost damage to pear flowers by application of gibberellin*, Plant Growth Regulation January, 2005, 45:1, 21-27; Izvest. Akad. Nauk. Latviiskoi SSR8: 117-126, Biol. Abstr. 46:44369, 1965; Proc. Am. Soc. Hort. Sci. 88: 197-203; and Loo, S. W., W. H. Hwang, &H. F. Tang. 1963. *Further studies on the effect of gibberellin on cold resistance of vegetables*. Acta Biol. Exp. Sinica, 8(2): 150-154, Biol. Abstr. 45:39260. 1964. The potential ability of gibberellins, and specifically GA3, to improve cereal grains' cold temperature recovery and grain yields has not been previously demonstrated or suggested.

In one embodiment, the present invention is directed to methods for improving cold temperature damage recovery of a cereal grain comprising applying an effective amount of at least one gibberellin to the cereal grain during the early vegetative growth stage.

In a preferred embodiment, the cereal grains are corn, rice, wheat, barley, sorghum, millet, oats, triticale, rye, buckwheat, fonio, or quinoa. In a more preferred embodiment, the cereal grains are corn, rice, wheat, or sorghum. In another preferred embodiment, the cereal grain is corn. Preferably the corn is popcorn, field corn or sweet corn. The cereal grain of the present invention may be genetically modified (GM) or non-GM.

In an embodiment, the gibberellin is gibberellin 1, GA3, gibberellin 4, gibberellin 7, or a combination thereof. In a preferred embodiment, the gibberellin is GA3 or a combination of gibberellin 4 and 7. In another preferred embodiment, the gibberellin is GA3.

In a further embodiment, the cereal grain is corn and the early vegetative growth stage is during the V1 to V6 growth stage. In a preferred embodiment, the growth stage is V2 to V3. In a most preferred embodiment, the growth stage is V2.

In an embodiment, the effective amount is from about 1 to 30 grams of gibberellin per hectare. In a preferred embodiment, the effective amount is from about 3 to 20 grams of gibberellin per hectare. In a more preferred embodiment, the effective amount is from about 6 to 16 grams of gibberellin per hectare. In a most preferred embodiment, the effective amount is from about 8 to 16 grams of gibberellin per hectare. In a preferred embodiment, GA3 is applied at from about 1 to about 30, preferably from about 3 to about 20, from about 6 to about 16, and from about 8 to about 16 grams (from about 3.2 to about 6.4 grams of GA3 per acre) per hectare.

In another embodiment, the gibberellin is applied with at least one herbicide, fungicide, insecticide, fertilizer or plant growth regulator that is not a gibberellin. In a preferred embodiment, the gibberellin is applied with at least one plant growth regulator other than a gibberellin.

In another embodiment, the herbicides include, but are not limited to, glyphosate, mesotrione, halosulfuron, saflufenacil or dicamba.

In a further embodiment, the fungicides include, but are not limited to tetraconazole, metconazole, a strobilurin, or a combined strobilurin-azole product.

In another embodiment, the insecticides include, but are not limited to methylparathion, bifenthryn, esfenvalerate, chlorpyrifos, carbaryl or methomyl.

In yet another embodiment, the foliar fertilizers include, but are not limited to CoRoN (available from Helena Chemical), a controlled-release nitrogen, or BioForge (available from Stoller USA), which is largely N,N'-diformyl urea, or other micro nutrient-containing sprays.

In an embodiment, the plant growth regulators include, but are not limited to, abscisic acid, aminoethoxyvinylglycine, 6-benzyladenine, jasmonic acid, napthylacetic acid or salicylic acid. In a preferred embodiment the plant growth regulator is abscisic acid.

In yet another embodiment, the present invention is directed to methods for improving yield of a cereal grains exposed to damaging cold temperatures comprising applying an effective amount of at least one gibberellin to the cereal grain during early vegetative growth stage.

In a preferred embodiment, the cereal grains are corn, rice, wheat, barley, sorghum, millet, oats, triticale, rye, buckwheat, fonio, or quinoa. In a more preferred embodiment, the cereal grains are corn, rice, wheat, or sorghum. In another preferred embodiment, the cereal grain is corn. The corn may be popcorn, sweet corn, or field corn. The cereal grain of the present invention may be genetically modified (GM) or non-GM.

In an embodiment, the gibberellin is gibberellin 1, GA3, gibberellin 4, gibberellin 7, or a combination thereof. In a preferred embodiment, the gibberellin is GA3 or a combination of gibberellin 4 and 7. In another preferred embodiment, the gibberellin is GA3.

In a further embodiment, the cereal grain is corn and the early vegetative growth stage is during the V2 to V3 growth stage.

In another embodiment, the gibberellin is applied before the cold temperature damage occurs.

In yet another embodiment, the gibberellin is applied after the cold temperature damage occurs.

In an embodiment, the effective amount is from about 1 to 30 grams of gibberellin per hectare. In a preferred embodiment, the effective amount is from about 3 to 20 grams of gibberellin per hectare. In a more preferred embodiment, the effective amount is from about 6 to 16 grams of gibberellin per hectare. In a most preferred embodiment, the effective amount is from about 8 to 16 grams of gibberellin per hectare. In a preferred embodiment, GA3 is applied at from about 1 to about 30, preferably from about 3 to about 20, from about 6 to about 16, and from about 8 to about 16 grams (from about 3.2 to about 6.4 grams of GA3 per acre) per hectare.

In another embodiment, the gibberellin is applied with at least one herbicide, fungicide, insecticide, fertilizer or plant growth regulator that is not a gibberellin. In a preferred embodiment, the gibberellin is applied with at least one plant growth regulator other than a gibberellin.

In another embodiment, the herbicides include, but are not limited to glyphosate, mesotrione, halosulfuron, saflufenacil or dicamba.

In a further embodiment, the fungicides include, but are not limited to tetraconazole, metconazole, a strobilurin, or a combined strobilurin-azole product.

In another embodiment, the insecticides include, but are not limited to methylparathion, bifenthryn, esfenvalerate, chlorpyrifos, carbaryl or methomyl.

In yet another embodiment, the foliar fertilizers include, but are not limited to CoRoN (available from Helena Chemical), a controlled-release nitrogen, or BioForge (available from Stoller USA), which is largely N,N'-diformyl urea, or other micro nutrient-containing sprays.

In an embodiment, the plant growth regulators include, but are not limited to abscisic acid, aminoethoxyvinylglycine, 6-benzyladenine, jasmonic acid, napthylacetic acid or salicylic acid.

The GA3 can be applied by any convenient means. Those skilled in the art are familiar with the modes of application that include foliar applications such as spraying, dusting, and granular applications; and soil applications including spraying, in-furrow treatments, or side-dressing. In a preferred embodiment, the GA3 is applied by spraying.

Aqueous spray solutions utilized in the present invention generally contain from about 0.01% to 0.5% (v/v) of a surface-active agent.

The surface active agent comprises at least one non-ionic surfactant. In general, the non-ionic surfactant may be any known non-ionic surfactant in the art. Suitable non-ionic surfactants are in general oligomers and polymers. Suitable polymers include alkyleneoxide random and block copolymers such as ethylene oxide-propylene oxide block copolymers (EO/PO block copolymers), including both EO-PO-EO and PO-EO-PO block copolymers; ethylene oxide-butylene oxide random and block copolymers, C2-6 alkyl adducts of ethylene oxide-propylene oxide random and block copolymers, C2-6 alkyl adducts of ethylene oxide-butylene oxide random and block copolymers, polyoxyethylene-polyoxypropylene monoalkylethers, such as methyl ether, ethyl ether, propyl ether, butyl ether or mixtures thereof; vinylacetate/vinylpyrrolidone copolymers; alkylated vinylpyrrolidone copolymers; polyvinylpyrrolidone; and polyalkyleneglycol, including the polypropylene glycols and polyethylene glycols. Other non-ionic agents are the lecithins; and silicone surface active agents (water soluble or dispersible surface active agents having a skeleton which comprises a siloxane chain e.g. Silwet® L77 polyalkyleneoxide modified heptamethyltrisiloxane, Silwet is a registered trademark of Helena Chemical Company). A suitable mixture in mineral oil is ATPLUS 411™ (available from Croda).

Applicants have referred to corn developmental stages throughout the application as "V" stages. The "V" stages are designated numerically as V1, V2, V3, etc. In this identification system of V(n), (n) represents the number of leaves with visible collars. Each leaf stage is defined according to the uppermost leaf whose leaf collar is visible. "VT" refers to tassel emergence growth stage and is not an early vegetative stage of corn.

As used herein, "cold damage" refers to temperatures low enough to damage the plants including when the plant tissue freezes due to a frost or freezing air temperatures. Cold damage may occur below 8 degrees Celsius. A freeze occurs at temperatures below 0 degrees Celsius. A frost may occur when temperatures are above freezing, but microclimate conditions (such as soil depressions, lack of soil heat radiation, wind, etc.) contribute to make near freezing air temperatures freeze the plant tissue and cause damage.

As used herein, "effective amount" refers to the amount of the gibberellin that will improve frost stress tolerance or improve yield. The "effective amount" will vary depending on the gibberellin concentration, the cereal(s) being treated, the severity of the frost, the result desired, and the life stage of the cereal(s), among other factors. Thus, it is not always possible to specify an exact "effective amount." However, an appropriate "effective amount" in any individual case may be determined by one of ordinary skill in the art.

As used herein, "cereal" or "cereal grain" refers to a cereal that is cultivated for the edible components of its grain. Cereals are members of either the monocot family Poaceae, Polygonaceae, or Amaranthaceae. Suitable examples of cereals include, but are not limited to, corn, rice, wheat, barley, sorghum, millet, oats, triticale, rye, buckwheat, fonio, and quinoa.

As used herein, "early vegetative growth stage" refers to the growth stage that begins at germination and ends when the plant is 50% of the mature plant size.

As used herein, "improving" means that the cereal grain has more of the quality than the cereal grain would have had it if it had not been treated by methods of the present invention.

The disclosed embodiments are simply exemplary embodiments of the inventive concepts disclosed herein and should not be considered as limiting, unless the claims expressly state otherwise.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a", "an" and "the" are intended to include the plural as well as the singular, unless the context clearly indicates otherwise.

The following examples are intended to illustrate the present invention and to teach one of ordinary skill in the art how to use the formulations of the invention. They are not intended to be limiting in any way.

EXAMPLES

Example 1

Hybrid corn was planted in several fields according to commercial practice. Subsequently, a frost occurred and frost damage was observed in many areas of the fields. RyzUp Smartgrass® 40% GA3 solution (1 gram of GA3/2.5 grams of product) was applied to areas with observed frost damage and areas without damage at rates of 0.21 oz/acre and 0.60 oz/acre (RyzUp Smartgrass is available from and a registered trademark of Valent BioSciences Corporation). The treatments were applied by a four-wheeler sprayer. The plants were about 2.5 to 3 inches tall at the time of application, at the V2 or V3 growth stages.

Nine days after the treatments, the height of 20 plants from each treatment and a control untreated group were measured. Ten of the plants were from a valley location (frost exposure) and ten plants from a hill location (no frost exposure). Heights were measured at the apex of the uppermost leaf. Applicant unexpectedly found that the untreated plants had a height of 11.1 centimeters, the 0.21 oz/acre treatment had a height of 16.9 centimeters, and the 0.6 oz/acre treatment had a height of 18.6 centimeters. The plants that are taller should produce more corn/higher yield. The treated plants were visibly healthier with more green leaves and taller.

Further, at nine days past treatment, the plants were rated visually for anthocyanin accumulation. Of the untreated corn, about 65 percent of plants had anthocyanin accumulation (resulting in purple leaves). In contrast, only 5% of the treated plants had anthocyanin accumulation.

Example 2

Corn seeds were planted in 18 cell flats filled with Sunshine 900 mix. Osmocote Plus (cal mag) 16-8-12 and Gypsum (CaCO2, MgCO2) were added (standard medium). The plants were watered and fertilized with 100 ppm of a commercially available 15-5-15 mixture plus 100 ppm calcium and 100 ppm magnesium, pH 6.5, as necessary and grown in the greenhouse.

After the corn grew for 7 days, the plants received a foliar application of 1.8 ml of 120 mg/liter GA3 plus 0.05% non-ionic surfactant per plant. Sixteen hours later, the GA3-treated and untreated control plants were moved to a cold room with temperature at −2° C. for 8 hours to simulate a freeze event. Plants were then moved to the greenhouse (25° C.). The plant height, number of injured leaves, and damaged leaf area were evaluated at 8 days after freezing. Results are shown below in Table 1. The pre-frost GA3 treatment did not reduce the number of injured leaves or damaged leaf area, but did help the corn recover from the frost damage.

TABLE 1

Effect of GA3 Treatment on Corn Exposed to Below Freezing Temperatures

| Treatments | Plant height (cm) | Number of injured leaf | Damaged leaf area (%) |
| --- | --- | --- | --- |
| Control, Frost treatment (−2° C. for 8 h) | 52.7 | 2.4 | 5.5 |
| 120 mg/liter GA3 Frost treatment (−2° C. for 8 h) | 59.7 | 2.6 | 12.4 |

Example 3

Corn seeds were planted in 2 quart pots filled with standard medium and grown in the greenhouse.

After the corn grew for 10 days at 24° C., it was at the V2 growth stage. The 10d post-sowing plants received a foliar application of 1.8 ml of 120 mg/liter GA3 plus 0.05% of a non-ionic surfactant. Immediately after spraying, both the GA3-treated and untreated control plants were moved to a growth chamber set at 8° C. with a 12:12 photoperiod. The height of the plants was measured one week after treatment. Results are shown below in Table 2.

TABLE 2

Effect of GA3 application on Corn growth at 8° C. for 7 d

| Treatment | Height at Application (cm) | Height at 7 d (cm) | Growth rate cm/day |
|---|---|---|---|
| Control | 23.9 | 27.8 | 0.55 |
| GA3 120 mg/liter (0.2 mg/plant: 6.9 grams of GA3/acre) | 23.9 | 28.0 | 0.58 |

The invention claimed is:

1. A method of reducing cold damage of corn comprising applying from about 6 to 16 grams per hectare of gibberellin 3 (GA3) to the corn during early vegetative growth stage.

2. The method of claim 1 wherein the early vegetative growth stage is during the V2 to V3 growth stage.

3. The method of claim 1 wherein from about 8 to 16 grams of the gibberellin is applied per hectare.

4. The method of claim 1 wherein the GA3 is applied with at least one herbicide, fungicide, insecticide, fertilizer or plant growth regulator that is not a gibberellin.

5. The method of claim 4 wherein the GA3 is applied with a plant growth regulator other than a gibberellin.

6. A method of improving yield of corn exposed to cold damaging temperatures comprising applying from about 6 to 16 grams per hectare of gibberellin 3 (GA3) to the corn during early vegetative growth stage.

7. The method of claim 6 wherein the early vegetative growth stage is during the V2 to V3 growth stage.

8. The method of claim 6 wherein the GA3 is applied with at least one herbicide, fungicide, insecticide, fertilizer or plant growth regulator that is not a gibberellin.

* * * * *